US012728246B2

(12) United States Patent
Lee

(10) Patent No.: US 12,728,246 B2
(45) Date of Patent: Sep. 8, 2026

(54) SKIN CARE DEVICE AND TIP FOR HANDPIECE OF THE SKIN CARE DEVICE

(71) Applicant: Dong Shin Lee, Hwaseong-si (KR)

(72) Inventor: Dong Shin Lee, Hwaseong-si (KR)

( * ) Notice: Subject to any disclaimer, the term of this patent is extended or adjusted under 35 U.S.C. 154(b) by 331 days.

(21) Appl. No.: 18/526,483

(22) Filed: Dec. 1, 2023

(65) Prior Publication Data

US 2024/0181233 A1 Jun. 6, 2024

(30) Foreign Application Priority Data

Dec. 2, 2022 (KR) ........................ 10-2022-0166496

(51) Int. Cl.
*A61M 35/00* (2006.01)
*A61M 11/00* (2006.01)

(52) U.S. Cl.
CPC ........ *A61M 35/003* (2013.01); *A61M 11/006* (2014.02); *A61M 2205/3389* (2013.01)

(58) Field of Classification Search
CPC .. A61M 35/003; A61M 11/006; A61M 35/00; A61H 9/0028; A61H 7/005; A45D 2200/057; A45D 34/00; A45D 44/00; A61N 5/0616; A65N 5/616
See application file for complete search history.

(56) References Cited

U.S. PATENT DOCUMENTS 8,048,089 B2 11/2011 Ignon et al.
2013/0103052 A1* 4/2013 Hull, Jr. ............. A61B 17/3205 606/131
2016/0038183 A1* 2/2016 Ignon ..................... A61B 50/22 606/131
2018/0303515 A1* 10/2018 Shadduck ...... A61B 17/320068
2022/0054810 A1* 2/2022 Lee ........................ A45D 34/04
(Continued)

FOREIGN PATENT DOCUMENTS

KR 10-2014-0020744 A 2/2014
KR 10-2015-0106696 A 9/2015
(Continued)

OTHER PUBLICATIONS

The extended European search report dated May 7, 2024 for corresponding European Patent Application No. 23213705.9 (8 pages).

(Continued)

*Primary Examiner* — Catharine L Anderson
*Assistant Examiner* — Meagan Ngo
(74) *Attorney, Agent, or Firm* — Hauptman Ham, LLP

(57) ABSTRACT

A skin care device comprising a tip is proposed. The tip may include a tip housing, a separation wall, and flow path partitions. The tip housing has a first side engaged with a handpiece of the skin care device, and a second side having a contact end inclined inward to contact a skin. The separation wall may be perpendicular to an inner peripheral surface of the second side of the tip housing, and may include spray ports for spraying a skin care solution and a suction port for sucking the sprayed skin care solution together with skin waste. The flow path partitions may be perpendicular to an outer surface of the separation wall, forming a flow path in a zigzag form from the spray ports toward the suction port. The flow path partitions may be concave with a center of the tip housing as a lowest point.

6 Claims, 2 Drawing Sheets

(56) References Cited

U.S. PATENT DOCUMENTS

2023/0033761 A1* 2/2023 Ignon .................... A61B 90/90
2025/0161642 A1* 5/2025 Ignon .................. A61B 17/545

FOREIGN PATENT DOCUMENTS

KR 10-1655775 B1 9/2016
KR 101688841 B1 * 12/2016 ............ A61B 17/50
KR 10-1798099 B1 12/2017
KR 10-1892988 B1 8/2018
KR 10-2019-0091916 A 8/2019
KR 10-2057766 B1 12/2019
KR 10-2021-0153955 A 12/2021
KR 20210153955 A * 12/2021 .......... A61H 9/0028

OTHER PUBLICATIONS

Office Action issued on Jul. 19, 2023, for corresponding Korean Patent Application No. 10-2022-0166496, along with an English machine translation (10 pages).

* cited by examiner

SKIN CARE DEVICE AND TIP FOR HANDPIECE OF THE SKIN CARE DEVICE

CROSS REFERENCE TO RELATED APPLICATION

The present application claims priority to Korean Patent Application No. 10-2022-0166496 filed Dec. 2, 2022, the entire contents of which are incorporated herein for all purposes by this reference.

BACKGROUND

Technical Field

The disclosure relates to a skin care device. In particular, the disclosure relates to a tip for a handpiece of a skin care device that increases skin care efficiency and prevents leakage of a skin care solution, and to a skin care device including the same.

Description of Related Technology

Generally, waste materials such as dead skin cells on the surface of the skin clog pores, adversely affecting skin health and beauty. Therefore, it is necessary to periodically remove waste from the skin. A skin care device is used for this need.

SUMMARY

One aspect is a tip for a skin care device handpiece that can adhere closely to the skin and thereby prevent leakage of a skin care solution, and a skin care device including the same.

Another aspect is a tip for a skin care device handpiece that can maximize skin care efficiency, and a skin care device including the same.

Another aspect is a tip for a handpiece of a skin care device that may include a tip housing, a separation wall, and a plurality of flow path partitions. The tip housing may include one side engaged with the handpiece of the skin care device, and other side having a contact end formed in a shape inclined inward to contact a skin. The separation wall may be formed perpendicularly to an inner peripheral surface of the other side of the tip housing, and may have spray ports for spraying a skin care solution and a suction port for sucking the sprayed skin care solution together with skin waste. The plurality of flow path partitions may be formed perpendicularly to an outer surface of the separation wall, may form a flow path in a zigzag form from the spray ports toward the suction port, and may be formed concavely with a center of the tip housing as a lowest point. A thickness of the plurality of flow path partitions may become thinner toward a top, and a height of the plurality of flow path partitions may be lower than a height of the tip housing.

In certain embodiments, the tip housing may have a cross-section of an oval shape.

In certain embodiments, the spray holes may include a first spray hole located near an edge of the separation wall and a second spray hole located symmetrically with the first spray hole. The suction port may be located in a center of the separation wall.

In certain embodiments, the plurality of flow path partitions may be arranged staggered to each other in parallel while one side of each flow path partition is in contact with an inner peripheral surface of the tip housing.

Another aspect is a skin care device that may include a main body, a handpiece, and a tip. The main body may include a supply unit, a recovery unit, and a control unit. The supply unit may be configured to store a skin care solution therein and supply the skin care solution. The recovery unit may be configured to recover the skin care solution and skin waste and store the recovered skin care solution and skin waste therein. The control unit may be configured to control supply and recovery of the skin care solution. The handpiece may be connected to the main body, may have a handheld form allowing a user to hold and use, and may include a supply conduit connected to the supply unit and a recovery conduit connected to the recovery unit. The tip may be combined with an end of the handpiece. Details of the tip may be as described above.

In certain embodiments, the recovery unit may include a sensor that detects a level of the recovered skin care solution. When the sensor detects that the recovered skin care solution reaches a predetermined level or more, the control unit may stop the supply and recovery of the skin care solution. The main body may further include a touch screen that displays the level of the skin care solution recovered in the recovery unit or displays an alarm message when the skin care solution recovered in the recovery unit reaches the predetermined level.

According to embodiments of the disclosure, the plurality of flow path partitions may be formed to have heights lower than or equal to the height of the tip housing, and may also be formed concavely with the center of the tip housing as the lowest point. Therefore, the tip for the skin care device handpiece can prevent leakage of the skin care solution by being in close contact with the skin.

In addition, the plurality of flow path partitions can guide the skin care solution to flow in a zigzag form from the spray port toward the suction port. Therefore, this arrangement of the flow path partitions can increase the contact time and contact area between the skin care solution and the skin, thus maximizing skin care efficiency.

BRIEF DESCRIPTION OF THE DRAWINGS

FIG. 1 is a block diagram of a skin care device according to the disclosure.

FIG. 2 is a perspective view showing a tip for a skin care device handpiece according to an embodiment of the disclosure.

DETAILED DESCRIPTION

Figures 3, 4:
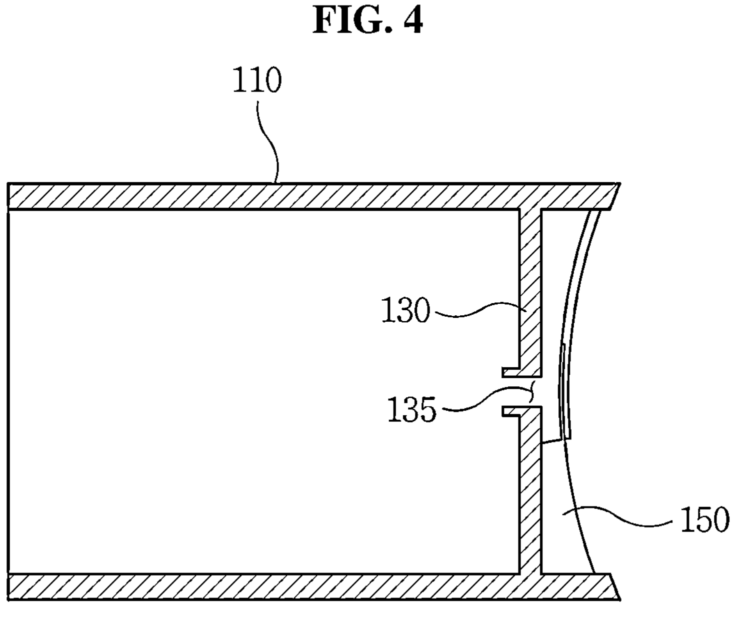
FIG. 3 is a cross-sectional view taken along line 3-3 in FIG. 2.
FIG. 4 is a cross-sectional view taken along line 4-4 in FIG. 2.

A skin care device includes a handpiece, and a tip to contact the skin is formed at the end of the handpiece. While the tip is moving in contact with the skin, the skin care device can spray a skin care solution onto the skin through a spray port formed on the tip, and also suck the sprayed skin care solution together with skin waste. As such, the skin care device is capable of efficiently cleansing the skin and removing skin waste.

However, since a typically used tip has a flat cross-section, the tip may not often adhere well to the skin when used in contact with the face composed of curved surfaces, causing a problem of skin care solution leaking.

In addition, a typically used tip has a short connection path between the spray port for spraying the skin care solution and the suction port for sucking the skin care solution. This causes problems that the skin care solution has a short contact time with the skin and the efficiency of skin cleansing and waste removal is low.

Hereinafter, various embodiments of the disclosure will be described in detail with reference to the accompanying drawings. The disclosure may, however, be embodied in many different forms and should not be construed as being limited to the embodiments set forth herein. Rather, these embodiments are provided so that the disclosure will be thorough and complete and will fully convey the scope of the disclosure to those skilled in the art.

In the following description of embodiments, techniques that are well known in the art and not directly related to the disclosure are not described. This is to clearly convey the subject matter of the disclosure by omitting an unnecessary explanation. In the disclosure, the same or corresponding elements are denoted by the same reference numerals.

Figures 1, 2:
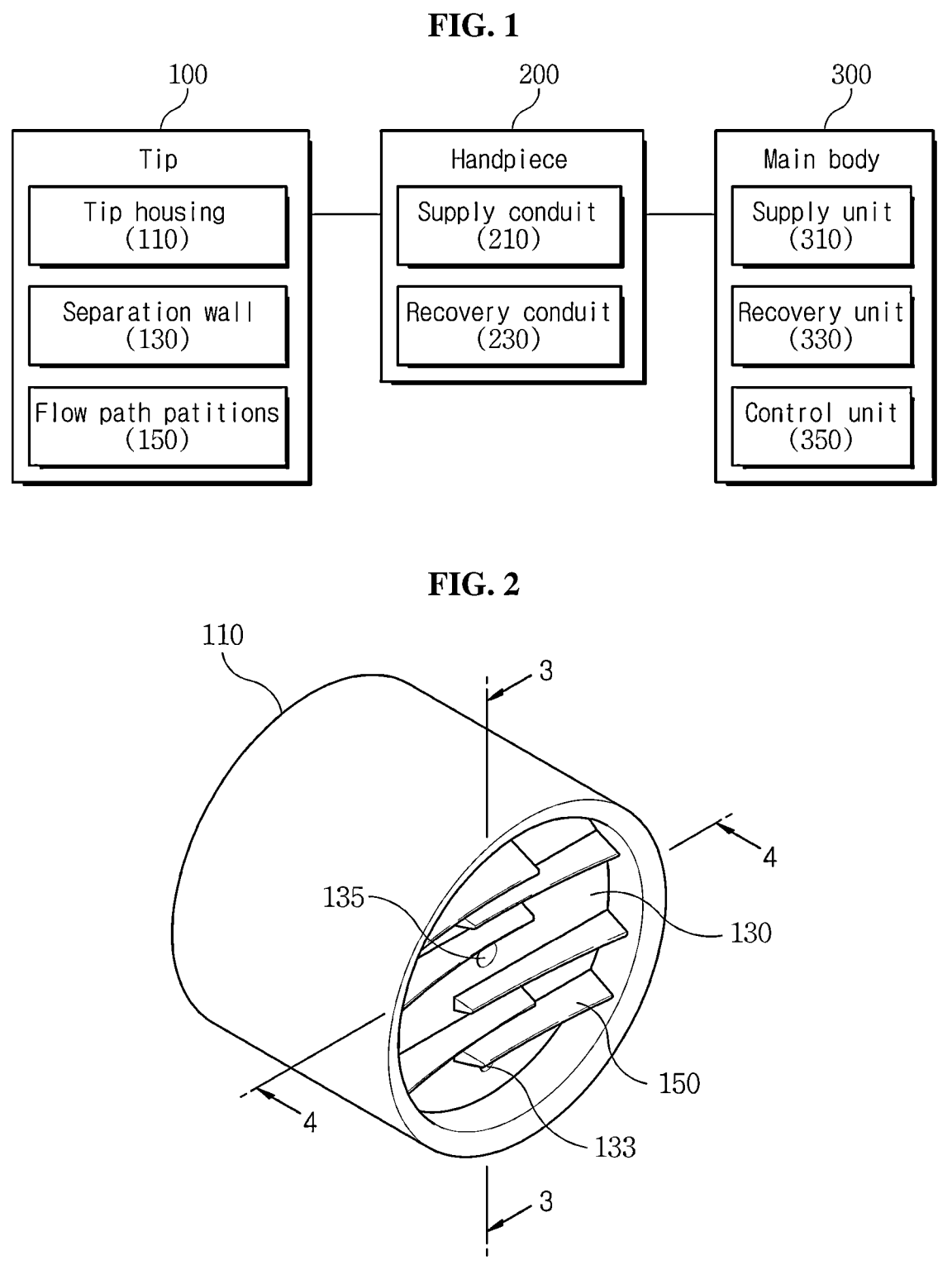

FIG. 1 is a block diagram of a skin care device according to the disclosure.

Referring to FIG. 1, the skin care device according to the disclosure includes a main body 300, a handpiece 200, and a tip 100. The main body 300 includes a supply unit 310, a recovery unit 330, and a control unit 350. The supply unit 310 is configured to store a skin care solution therein and supply it. The recovery unit 330 is configured to recover the skin care solution and skin waste and store them therein. The control unit 350 is configured to control the supply and recovery of the skin care solution. The handpiece 200 is connected to the main body 300 and includes a supply conduit 210 and a recovery conduit 230 formed therein. The supply conduit 210 is connected to the supply unit 310, and the recovery conduit 230 is connected to the recovery unit 330. The tip 100 is combined with the end of the handpiece 200.

Specifically, the main body 300 may be provided with a holder for holding the handpiece 200 on the outside and may include therein the supply unit 310, the recovery unit 330, and the control unit 350.

The supply unit 310 may include a supply container that stores the skin care solution to be sprayed, and a supply pump that creates pressure for spraying the skin care solution onto the skin.

The recovery unit 330 may include a recovery container that stores the skin care solution and skin waste recovered from the skin, a recovery pump that creates pressure for recovering the skin care solution from the skin, and a sensor that detects the level of the skin care solution collected in the recovery container.

The control unit 350 can generally control the supply and recovery process of the skin care solution, such as the supply pressure, supply time, recovery pressure, and recovery time of the skin care solution. Additionally, when the sensor detects that the recovered skin care solution reaches a predetermined level or more, the control unit 350 can stop the supply and recovery process of the skin care solution to prevent backflow of the recovered skin care solution.

In addition, the main body 300 may further include an analog type dial or touch screen that receives a control input from the user. In particular, the touch screen may display the level of the skin care solution collected in the recovery container and/or display an alarm message indicating that the skin care solution collected in the recovery container reaches a predetermined level.

The handpiece 200 is a handheld tool that the user can hold and use, and may include the supply conduit 210 and the recovery conduit 230 formed therein. The supply conduit 210 connects the supply container and the tip 100, and the recovery conduit 230 connects the recovery container and the tip 100, thus both allowing the skin care solution to be supplied and recovered through the tip 100.

The tip 100 may be detachably combined with the end of the handpiece 200 and is capable of contacting the skin for skin cleansing and removal of skin waste.

Hereinafter, the configuration of the tip 100 for the handpiece 200 of the skin care device according to an embodiment will be described in more detail.

FIG. 2 is a perspective view showing a tip for a skin care device handpiece according to an embodiment of the disclosure. FIG. 3 is a cross-sectional view taken along line 3-3 in FIG. 2, and FIG. 4 is a cross-sectional view taken along line 4-4 in FIG. 2.

Referring to FIGS. 2 to 4, the tip 100 for the handpiece of the skin care device includes a tip housing 110, a separation wall 130, and a plurality of flow path partitions 150. The tip housing 110 is combined with the handpiece of the skin care device. The separation wall 130 is formed perpendicularly to the inner peripheral surface of the tip housing 110 and has spray ports 131 and 133 and a suction port 135. The plurality of flow path partitions 150 are formed perpendicularly to the outer surface of the separation wall 130 and guide the skin care solution to flow in a zigzag form from the spray ports 131 and 133 toward the suction port 135.

The tip housing 110 may have a cylindrical shape with open both ends. One side of the tip housing 110 may have an engaging groove or engaging protrusion, so that it can be engaged with the handpiece of the skin care device. The other side of the tip housing 110 may have a contact end formed in a shape inclined toward the inside of the tip housing 110, so that it can smoothly contact the skin. The tip housing 110 may have a cross-section of, for example, an oval shape, but is not limited thereto. When the cross-section of the tip housing 110 is oval, the other side of the tip housing 110 in contact with the skin can be easily moved along narrow and curved portions of the face such as a portion between the eyebrows, a portion next to the nose, and a portion around the mouth.

The separation wall 130 is formed perpendicularly to the inner peripheral surface of the other side of the tip housing 110 to distinguish the inside and outside of the tip housing 110. In the separation wall 130, the spray ports 131 and 133 and the suction port 135 may be formed. The skin care solution can be sprayed through the spray ports 131 and 133 and then sucked together with skin waste through the suction port 135.

The spray holes 131 and 133 may include a first spray hole 131 located near the edge of the separation wall 130 and a second spray hole 133 located symmetrically with the first spray hole 131. For example, when the separation wall 130 is oval-shaped, the first and second spray holes 131 and 133 may be symmetrically located on the long or short diameter of the oval, but are not limited thereto.

The suction port 135 may be located in the center of the separation wall 130. For example, when the separation wall 130 is oval-shaped, the suction port 135 may be located at the center of the oval, but is not limited thereto.

The plurality of flow path partitions 150 may be formed perpendicularly to the outer surface of the separation wall 130. In order to guide the skin care solution to flow in a zigzag form from the spray ports 131 and 133 toward the suction port 135, the plurality of flow path partitions 150 may be arranged staggered to each other in parallel while one side of each flow path partition 150 is in contact with the inner peripheral surface of the tip housing 110. However, the arrangement of the flow path partitions 150 is not limited to the above example and may alternatively have a concentric circular shape or a spiral shape. Such arrangement of the flow path partitions 150 can increase the contact time between the skin care solution and the skin, thus maximizing skin care efficiency.

Additionally, the thickness of each flow path partition 150 may become thinner toward the top, thereby increasing the contact area between the skin care solution and the skin and maximizing skin care efficiency.

The plurality of flow path partitions 150 may be formed to have heights lower than or equal to the height of the tip housing 110, and may be formed concavely with the center of the tip housing 110 as a lowest point. Therefore, the tip 100 for the skin care device handpiece can prevent leakage of the skin care solution by being in close contact with the skin.

While the disclosure has been particularly shown and described with reference to exemplary embodiments thereof, it will be understood by those skilled in the art that various changes in form and details may be made therein without departing from the scope of the disclosure as defined by the appended claims.

What is claimed is:

1. A tip for a handpiece of a skin care device, the tip comprising:

a tip housing including:

a first side engaged with the handpiece of the skin care device, and a second side comprising a contact end configured to contact a skin;

a separation wall perpendicular to an inner peripheral surface of the second side of the tip housing, the separation wall comprising:

spray ports configured to spray a skin care solution, and a suction port configured to suck the sprayed skin care solution together with skin waste; and a plurality of flow path partitions perpendicular to an outer surface of the separation wall, configured to form a flow path in a zigzag form from the spray ports toward the suction port, and being concave with a center of the tip housing as a lowest point, wherein a thickness of the plurality of flow path partitions becomes thinner toward a top, and a height of the plurality of flow path partitions is lower than a height of the tip housing, and wherein the plurality of flow path partitions is arranged staggered to each other in parallel while one side of each flow path partition is in contact with an inner peripheral surface of the tip housing.

2. The tip of claim 1, wherein the tip housing has a cross-section of an oval shape.

3. The tip of claim 1, wherein the spray holes include a first spray hole located adjacent to an edge of the separation wall and a second spray hole located symmetrically with the first spray hole, and wherein the suction port is located in a center of the separation wall.

4. The tip of claim 1, wherein the contact end of the tip housing is inclined inward.

5. A skin care device comprising:

a main body including:

a supply unit configured to store a skin care solution therein and supply the skin care solution, a recovery unit configured to recover the skin care solution and skin waste and store the recovered skin care solution and skin waste therein, and a controller configured to control supply and recovery of the skin care solution;

a handpiece connected to the main body, having a hand-held form allowing a user to hold and use, and including a supply conduit connected to the supply unit and a recovery conduit connected to the recovery unit; and a tip combined with an end of the handpiece, wherein the tip comprises:

a tip housing including:

a first side engaged with the handpiece of the skin care device, and a second side comprising a contact end configured to contact a skin;

a separation wall perpendicular to an inner peripheral surface of the second side of the tip housing, the separation wall comprising:

spray ports configured to spray the skin care solution, and a suction port configured to suck the sprayed skin care solution together with skin waste; and a plurality of flow path partitions perpendicular to an outer surface of the separation wall, configured to form a flow path in a zigzag form from the spray ports toward the suction port, and being concave with a center of the tip housing as a lowest point, wherein a thickness of the plurality of flow path partitions becomes thinner toward a top, and a height of the plurality of flow path partitions is lower than a height of the tip housing, and wherein the plurality of flow path partitions is arranged staggered to each other in parallel while one side of each flow path partition is in contact with an inner peripheral surface of the tip housing.

6. The skin care device of claim 5, wherein the recovery unit includes a sensor configured to detect a level of the recovered skin care solution, wherein in response to the sensor detecting that the recovered skin care solution reaches a predetermined level or more, the controller is configured to stop the supply and recovery of the skin care solution, and wherein the main body further includes a touch screen configured to display:

the level of the skin care solution recovered in the recovery unit or an alarm message in response to the skin care solution recovered in the recovery unit reaching the predetermined level.

* * * * *